(12) United States Patent
Tuma et al.

(10) Patent No.: US 8,308,663 B2
(45) Date of Patent: Nov. 13, 2012

(54) DEVICE AND METHOD FOR DETERMINING THE APERTURE ANGLE OF A JOINT

(75) Inventors: Gregor Tuma, München (DE); Mario Schubert, Landsham (DE); Claus Shaffrath, München (DE)

(73) Assignee: Brainlab AG, Feldkirchen (DE)

( * ) Notice: Subject to any disclaimer, the term of this patent is extended or adjusted under 35 U.S.C. 154(b) by 0 days.

(21) Appl. No.: 12/013,234

(22) Filed: Jan. 11, 2008

(65) Prior Publication Data

US 2008/0183104 A1    Jul. 31, 2008

Related U.S. Application Data

(63) Continuation of application No. 10/670,177, filed on Sep. 23, 2003, now abandoned.

(60) Provisional application No. 60/440,700, filed on Jan. 17, 2003.

(30) Foreign Application Priority Data

Sep. 24, 2002 (EP) .................................. 02 021 384

(51) Int. Cl.
*A61B 5/103* (2006.01)
*A61B 5/117* (2006.01)
(52) U.S. Cl. ........................................ 600/595; 600/587
(58) Field of Classification Search .................. 600/587, 600/594, 595
See application file for complete search history.

(56) References Cited

U.S. PATENT DOCUMENTS

| | | | |
|---|---|---|---|
| 4,804,000 A | 2/1989 | Lamb et al. |
| 5,197,488 A | 3/1993 | Kovacevic |
| 5,682,886 A | 11/1997 | Delp et al. |
| 6,002,859 A | 12/1999 | DiGioia, III et al. |
| 6,231,526 B1 | 5/2001 | Taylor et al. |
| 2002/0107522 A1 | 8/2002 | Picard et al. |

FOREIGN PATENT DOCUMENTS

WO    02/02028    1/2002

*Primary Examiner* — Jeffrey G Hoekstra
(74) *Attorney, Agent, or Firm* — Renner, Otto, Boisselle & Sklar, LLP

(57) ABSTRACT

A device for determining the aperture angle of a joint includes a detection device for detecting positions of joint components and/or positions of structures connected to or to be connected to the joint and a computational unit for ascertaining the aperture angle of the joint based on the detected positions.

8 Claims, 3 Drawing Sheets

DEVICE AND METHOD FOR DETERMINING THE APERTURE ANGLE OF A JOINT

RELATED APPLICATION DATA

This application is a continuation of U.S. application Ser. No. 10/670,177, filed on Sep. 23, 2003 now abandoned, which claims priority to U.S. Provisional Application No. 60/440,700, filed on Jan. 17, 2003, both of which are incorporated herein by reference in their entireties.

FIELD OF THE INVENTION

The present invention relates to a device and a method for determining the aperture angle of a joint lying between two body structures.

BACKGROUND OF THE INVENTION

Artificial hip joints are known in which a femur implant is introduced into a bodily femur, after a head of the bodily joint has been removed. A joint cavity is introduced into the hip as a counter bearing, which, as an abutment, can accommodate a spherical or partially spherical head of the femur implant. Seating the implants precisely is a fundamental criterion for successfully implanting a hip joint. Even the smallest deviations can lead to excessively rapid wear and tear and, therefore, to a short service life of the hip joint implant. In the event of a sudden stress, such as, for example, an impact, a hip implant, which is not introduced precisely, can easily be dislocated or loosened. Therefore, it is advantageous to intraoperatively verify that an implanted joint is correctly seated and positioned.

It is known that, while implanting a hip joint, a surgeon manually moves a patient's leg in various directions until it is prevented from moving further by the patient's anatomy, the implanted components meeting adjacent bones, or encumbrances by tissues or ligaments. An experienced surgeon uses this manual movement to assess the flexibility of the joint and, therefore, how to correctly seat the individual components of an implanted joint. However, a surgeon can only very roughly assess whether flexibility ascertained and assessed in this way is sufficient for the patient's daily life.

A device and a method for determining the position of a component of an implant are known from U.S. Pat. No. 6,002, 859, in which a model of the joint and the implant components are generated and a movement of the joint is simulated using the models.

SUMMARY OF THE INVENTION

According to one aspect, the invention relates to determining an aperture angle of a joint lying between two body structures, such as, for example, the aperture angle of a hip joint, a knee joint, an elbow joint or other joints. It is to be appreciated that the term "aperture angle" is intended to be understood, for example, in the case of the ball joint-like hip joint, both as the angle between a fixed upper leg axis and a plane or axis defined by the position of the hip, and as the spatial position or orientation of the angle. The intention is, for example, to ascertain how far the femur is inclined forwards, backwards or to the side, relative for example to the hip, i.e. the spatial angle which the joint forms is determined. The intention is also, for example, to ascertain how a joint or parts or structures thereof are rotated, for example, about a center axis.

It is an object of the present invention to propose a device and a method for determining the aperture angle of a joint, which can be used to precisely verify whether implant components are correctly seated.

In one embodiment, the device for determining the aperture angle of a joint, such as, for example, a natural or an artificial joint, and/or for determining relative positions of components or structures, can be used before, while and after a joint implant is implanted in order, for example, to intraoperatively ascertain the aperture angle or the range of motion of a joint. If necessary, the device can be used to make modifications to the implanted joint components or the position of the joint component and/or to the patient's anatomy, e.g., by surgery. A detection device can be provided. The detection device can include, for example, a camera for detecting visible or infrared light, electromagnetic sensors (magnetic tracking), a sound sensor, or a system based on radio, using which the position of the components forming the joint and/or the structures connected to the joint or to be connected to the joint can be ascertained.

Changes in the position and/or the rotational position of one or more components or structures can be detected, such that, for example, the changes can be ascertained in six degrees of freedom. In this way, markers can be attached in a known way to the respective components forming the joint or to adjacent structures. For example, markers can be attached to the hip and the femur and/or to the implanted components, in order to detect the position of the respective structures or components once the corresponding elements, provided with markers, have been registered. Furthermore, a computational unit can be provided to which the positional signals ascertained by the detection device, such as, for example, the optically detected outlines of a structure or signals emitted for example by markers, and, therefore, the position of the elements or structures connected to these markers is supplied, in order to ascertain the aperture angle or the spatial angle in general of a joint or an angle formed by two structures from this information.

The device in accordance with the invention thus enables an improvement in verifying and assessing, and, therefore, in performing, the implantation of an artificial joint, such that the outcome of implantation can be improved. Positional values and angular values can be automatically ascertained, in order, for example, to verify that a joint is correctly seated using movements performed manually or automatically, for example, using robots. Taking into account anatomically relevant influencing parameters, such as the ligaments, soft tissues, etc., it can be ascertained whether movements, which may be performed using the implanted joint, are sufficient or whether the implant or the seating of the implant still has to be changed, in order to obtain the desired range of motion of the joint. A joint can, for example, be moved in each direction until it is no longer possible, using normal force, to open or close the joint further due to it colliding with a body structure or a component of the joint or due to other factors, such that the range of motion of the joint can be ascertained in various directions. Precise angular values can be ascertained by the device in accordance with the invention, which can be compared, for example, with predetermined reference values, to verify the correct seating or the correct functionality of a joint, without being reliant on the experience of a surgeon.

Thus, in accordance with the invention, the actual positions of the joint components and/or of the body structures connected to the joint, such as, for example, the hip and the femur, can be ascertained three-dimensionally, even intra-operatively. In addition, their position relative to each other can be determined, such that the aperture angle of the joint can be precisely measured in various directions or the six degrees of freedom determining the spatial position and orientation can be precisely measured.

A data output device, such as a display for outputting the ascertained aperture angle of the joint or a screen, can be provided. The three-dimensional spatial position of the joint can be shown together on the data output device with the parameters describing the position of the joint, such as, for example, the aperture angle and the spatial position of the aperture angle.

In one embodiment, the device for determining the aperture angle of a joint can include a device for applying defined forces onto the joint or a particular joint component in defined directions. For example, the device for applying defined forces can include a robot or a manually-operable device, which can display an applied force, in order to be able to ascertain how far a joint is moved when particular forces are applied. This can be used to obtain defined measurements, which can, for example, be compared with previously recorded reference values.

In accordance with another embodiment of the invention, a method for determining the aperture angle of a joint includes detecting the position of the structures forming the joint and ascertaining the aperture angle from the detected positions. The method can, for example, be used intra-operatively, to measure the aperture angle or the flexibility in general of a joint during or after surgery, so as to provide information to assist the surgeon's work. No surgery is necessary to perform the method since only the position of the components forming the joint and/or of the adjacent body structures are recorded. This can be accomplished, for example, using attached markers, by detecting the outlines or using other suitable methods, and the aperture angle is calculated from the information recorded in this way.

Recordings of the natural or artificial joint and/or of body structures adjacent to the joint can be used to determine the aperture angle or spatial angle of a joint, wherein nuclear spin resonance (MR) methods, computer tomography (CT) methods, ultrasound methods or other suitable methods can be used. The recorded body structures can be sub-divided into individual elements, for example, using known segmentation or separating methods. In this way, the borders of adjacent structures can be obtained from the recorded data, in order to have data for calculating the aperture angle from positional data of the body structures or for calculating an optimum position for a joint to be implanted. In general, bone structures are detected in an image data set in a way that is substantially dependent on how the patient is positioned or lying at the time the image data are detected. There are rough instructions for radiology and for the patient with respect to a desired position for recording the image data set. However, the variable positions of the individual bone structures can be virtually moved to an initial position or neutral position to be defined, to provide a precise basis for comparison, which also enables comparison between a number of patients.

After segmenting, three local co-ordinate systems can be defined, such as, for example, Femur Left, Femur Right and Pelvis. These can then be oriented with respect to each other in accordance with a fixed specification and can thus be moved into a defined positional relationship. If one then wishes to visualize positional data, such as, for example, angles, length of leg or of a joint, then this neutral position can be used as a starting position with respect to which an aperture angle or a spatial position can be defined. In this way, initial conditions can be created, which may even be reproduced and compared with each other for various patients.

In one embodiment, an image data set can be recorded in an arbitrary position. By segmenting individual body structures, for example, Hip, Femur Left and Femur Right can be identified as individual elements. Coordinate systems can be assigned to the individual, segmented structures, where the coordinate systems enable the structures to be virtually aligned in the neutral position.

Reference elements, such as, for example, reflective markers, can be attached to the joint to be implanted. In one embodiment, the reference elements can be attached to the individual components of the joint and/or to the body structures adjacent to the joint. This enables one to ascertain and track the spatial position of the joint or of the individual joint components and/or the corresponding body structures, once the respective elements have been registered. As such, the spatial positions of the individual joint components and/or the spatial positions of the body structure adjacent to the joint are available, for example, for ascertaining a possible range of motion of a joint.

The parameters indicative of the spatial position and the aperture angle of the joint can be visualized, such that it is possible, preferably in real time, to see what angle currently exists.

In accordance with one embodiment, data describing the flexibility of a natural or implanted joint can be measured and stored, such that at least one reference value is available, in order to be able to verify that a newly implanted joint is corrected seated and exhibits the desired flexibility. An implanted joint can, for example, be verified by comparing the measured flexibility of the implanted joint with measurement data from natural, i.e., not implanted, joints or successfully implanted joints. Due to symmetry, for example, in the case of a hip joint, comparative data of the opposite joint to the joint to be replaced can likewise be used to obtain reference data for positioning a joint to be implanted.

In one embodiment, defined forces can be applied to the joint in defined directions, in order to have comparative values for defined stresses on the joint, enabling an implanted joint to be verified.

In accordance with another aspect, the invention relates to a computer program which, when it is loaded onto a computer or run on a computer, performs at least one of the method steps described above. In accordance with another aspect, the invention relates to a storage medium for a program or a computer program product comprising such a program.

BRIEF DESCRIPTION OF THE DRAWINGS

These and further features of the present invention will be apparent with reference to the following description and drawings, wherein.

DETAILED DESCRIPTION OF THE INVENTION

The invention relates to a device and method for determining an aperture angle of a joint lying between two body structures, such as, for example, the aperture angle of a hip joint, a knee joint, an elbow joint or other joints. It is to be appreciated that the term "aperture angle" is intended to be understood, for example, in the case of the ball joint-like hip joint, both as the angle between a fixed upper leg axis and a plane or axis defined by the position of the hip, and as the spatial position or orientation of the angle. The intention is, for example, to ascertain how far the femur is inclined forwards, backwards or to the side, relative for example to the hip, i.e. the spatial angle which the joint forms is determined. The intention is also, for example, to ascertain how a joint or parts or structures thereof are rotated, for example, about a center axis.

Figure 1:
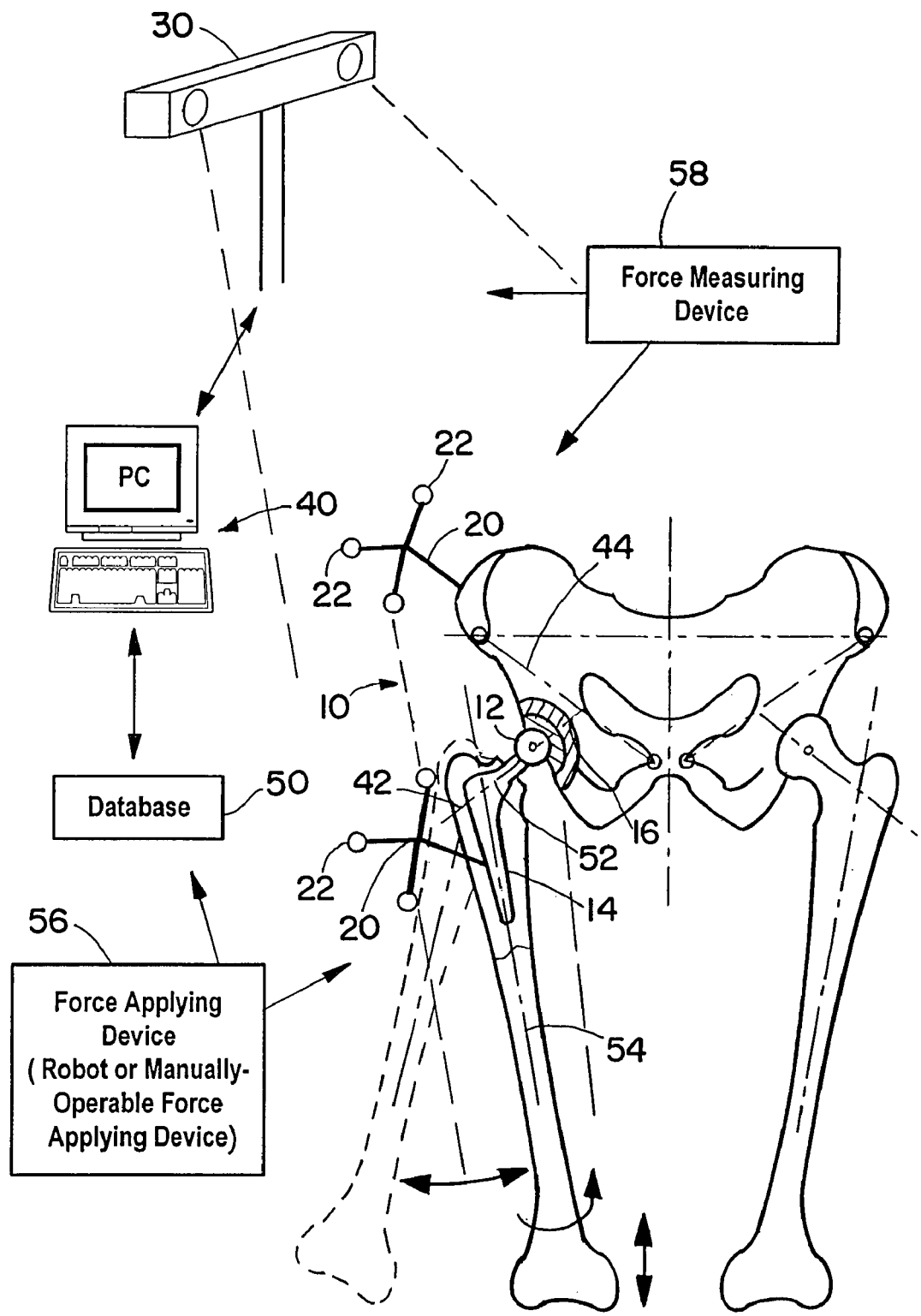
FIG. 1 is a schematic illustration of a device for determining the aperture angle of a joint in accordance with the invention.

FIG. 1 schematically shows an artificial hip joint 10 including a joint head 12 of a femur implant 14, which is accommodated by a joint cavity 16 of the hip. Reference elements or stars 20, which include markers 22 are attached to the body structures connected to the joint head 12 and the joint cavity 16, respectively, and/or to the joint head 12 and/or the joint cavity 16 themselves, in order to be able to determine the position of the joint head 12 and the joint cavity 16. An camera 30, such as an infra-red (IR) camera, records light reflected by the markers 22 of the reference stars 20 and forwards the signals to a computational unit 40.

The computational unit 40 can display the position and/or the spatial angle in the orthopaedically defined directions of abduction, adduction, flexion, extension, internal and external rotation and changes in leg length. It is also possible to calculate the angle between a previously defined axis 42 through the joint head 12 and a previously defined axis 44 through the joint cavity 16. For calculating the angle, it is possible, for example, to fall back on data stored in a data base 50, which includes, for example, information on the geometry of the joint head 12, the joint cavity 16, the fixing position of the reference stars 20 or other information. Furthermore, reference values for a series of measurements performed can be stored in the data base 50, where these values can be used for comparison with subsequent measurements. A robot 60 and a force measuring device 62 (both in communication with the computational unit 40) can be employed for applying forces in defined directions to the joint as well as measuring respective applied forces.

A coordinate system of the femur can, for example, be used as a reference system and can be defined by a plane formed by a neck axis 52 (i.e., the center axis of the neck of the femur) and a shaft axis 54 (i.e., the center axis of the long bone of the femur). This plane is oriented about the rotational point of the femur, parallel to the frontal pelvic plane.

The healthy, opposite joint or leg to the joint to be implanted can be used as a comparative reference for, for example, the range of motion to be enabled or for the length of the leg.

The spatial angle ascertained by the computational unit 40 can be outputted to a display unit, such as, for example, a screen, and there numerically outputted as a graphical representation of the joint and/or with additional information.

Figure 2:
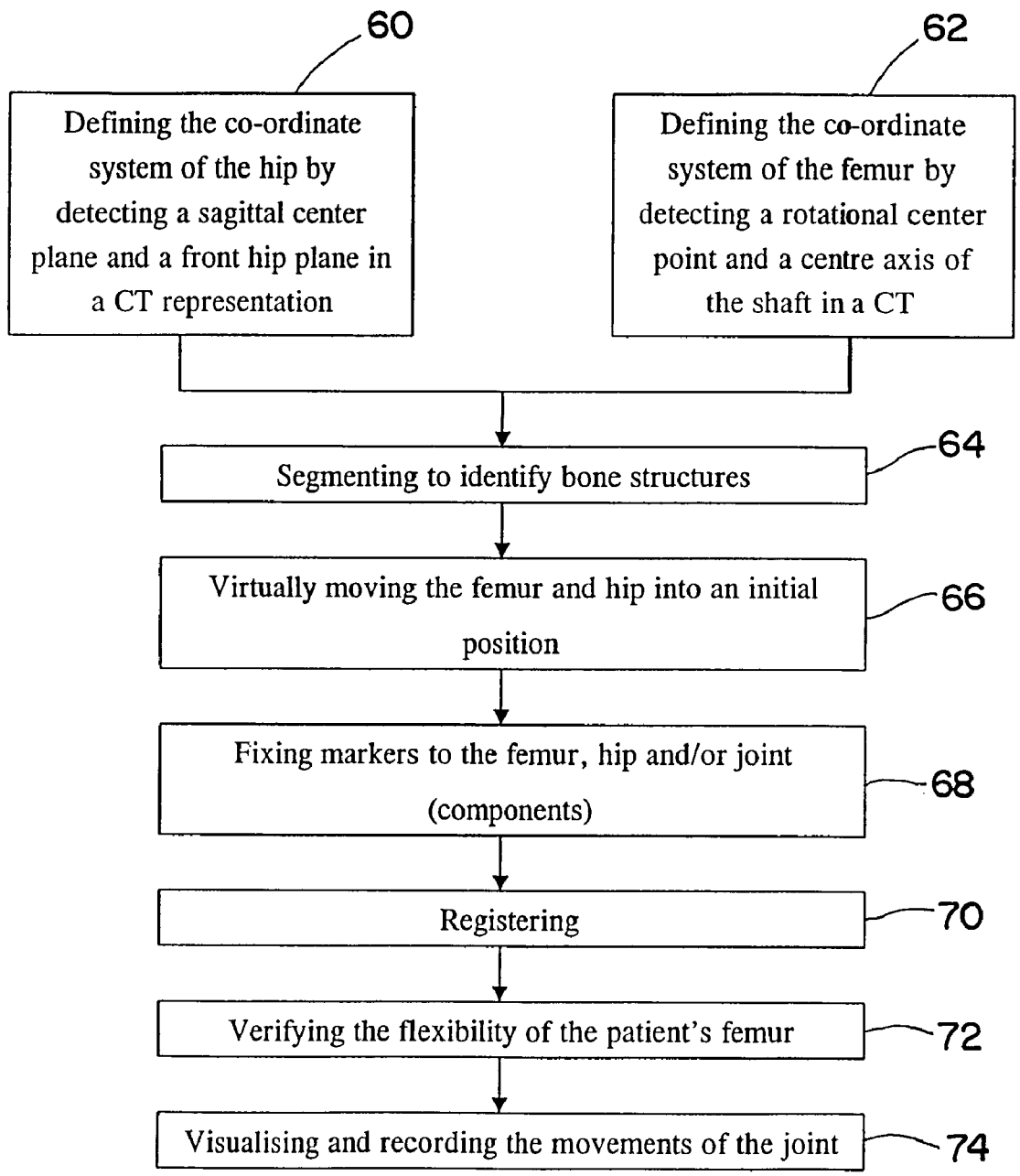
FIG. 2 is a flow chart illustrating a method of determining the aperture angle of a joint in accordance with the invention.

With reference now to FIG. 2, a method for determining the aperture angle of a hip joint is provided. It is to be appreciated that while FIG. 2 is described with reference to a hip joint, the methodology is applicable to other joints. In step 60, a co-ordinate system of the hip can be defined by identifying a sagittal center plane and a front hip plane in a computer tomographic (CT) representation. In step 62, a co-ordinate system of the femur is defined by identifying a rotational center point and a center axis in a computer tomographic representation. It is to be appreciated that steps 60 and 62 can be performed both simultaneously and sequentially, in any order, i.e., step 62 can also be performed before step 60.

In step 64, segmentation is performed, in order to be able to distinguish the individual bone structures, such as, for example, the hip, right femur and left femur, in the recordings of a body structure.

In step 66, a virtual movement of one or both femurs and the hip to a neutral or initial position is simulated in a simulation, wherein for example the coronal plane of the femur lies parallel to the front plane of the hip in an initial position, to define a zero position.

In step 68, markers, such as, for example, reference stars, can be attached to the femur and the hip and/or to the joint cavity and the joint head, on the side to be treated.

In step 70, the respective elements are then registered. In one embodiment, the registration can be performed using a navigation system as is described in co-owned U.S. Pat. No. 6,351,659, which is incorporated herein by reference in its entirety.

In step 72, the flexibility and/or the range of motion of a patient's femur is verified.

In step 74, the maximum possible movements, for example, expressed by aperture angles of the joint in various directions, are ascertained, visualized and recorded. In this way, an abduction (abducting or moving the joint backwards), adduction (guiding or moving the joint forwards), flexion (bending) and/or extension (stretching) of the hip joint or of another of a patient's joints can be performed. It is also possible to compare the movements possible with the flexibility of the patient's still healthy joint.

Optionally, the flexibility or range of motion of a patient's femur can be verified by comparing them with the flexibility or range of motion of a healthy joint lying symmetrical to said femur.

The joint can be moved both manually and automatically, for example using a robot, in order to apply defined forces to the joint in defined directions.

As described above, recordings of the natural or artificial joint and/or of body structures adjacent to the joint can be used to determine the aperture angle or spatial angle of a joint, wherein nuclear spin resonance (MR) methods, computer tomography (CT) methods, ultrasound methods or other suitable methods can be used. The recorded body structures can be sub-divided into individual elements, for example, using known segmentation or separating methods. In this way, the borders of adjacent structures can be obtained from the recorded data, in order to have data for calculating the aperture angle from positional data of the body structures or for calculating an optimum position for a joint to be implanted. In general, bone structures are detected in an image data set in a way that is substantially dependent on how the patient is positioned or lying at the time the image data are detected. There are rough instructions for radiology and for the patient with respect to a desired position for recording the image data set. However, the variable positions of the individual bone structures can be virtually moved to an initial position or neutral position to be defined, to provide a precise basis for comparison, which also enables comparison between a number of patients.

After segmenting, three local co-ordinate systems can be defined, such as, for example, Femur Left, Femur Right and Pelvis. These can then be oriented with respect to each other in accordance with a fixed specification and can thus be moved into a defined positional relationship. If one then wishes to visualize positional data, such as, for example, angles, length of leg or of a joint, then this neutral position can be used as a starting position with respect to which an aperture angle or a spatial position can be defined. In this way, initial conditions can be created, which may even be reproduced and compared with each other for various patients.

Figure 3A:
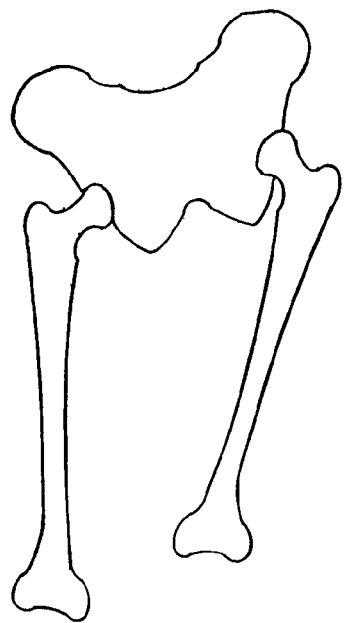
FIG. 3A-3D are schematic diagrams illustrating a method of determining a neutral position in accordance with the invention.
Figure 3B:
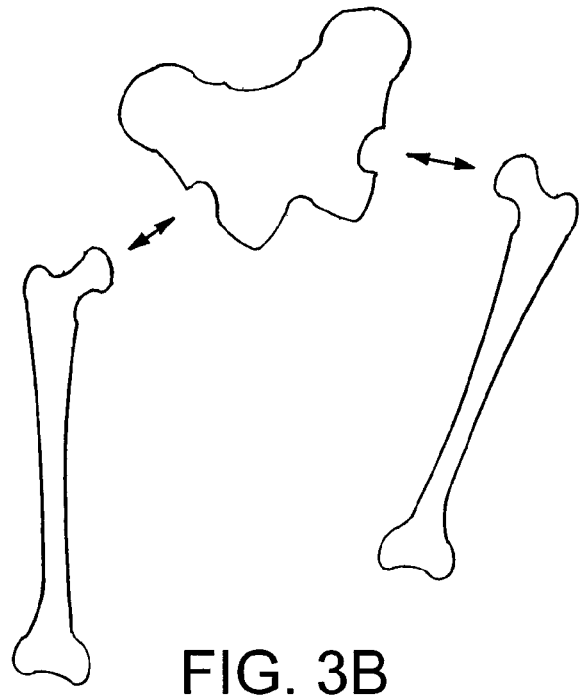
Figure 3C:
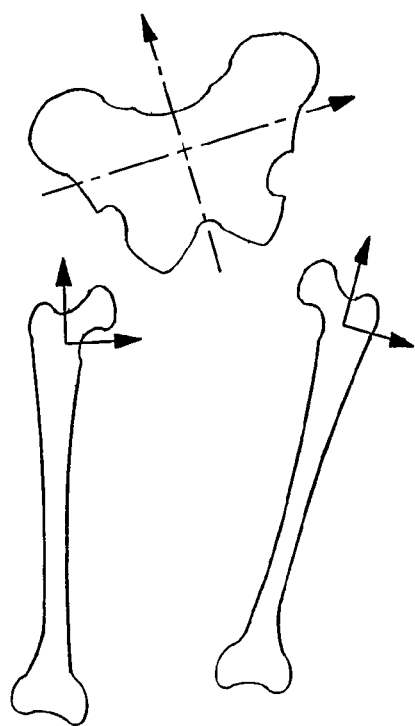
Figure 3D:
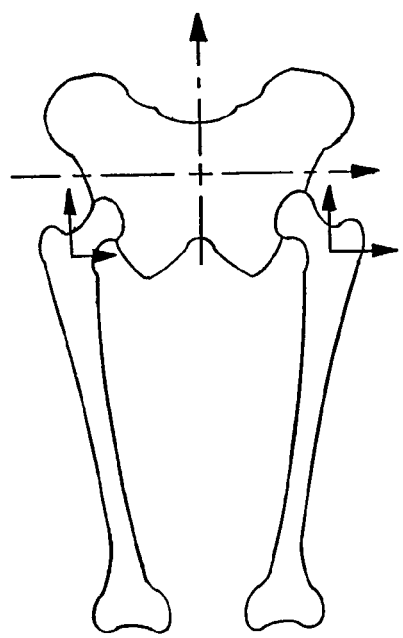

FIGS. 3A-3D illustrate the procedure described above. An image data set, which can be recorded in an arbitrary position of the patient, is shown schematically in FIG. 3A. By segmenting, as shown schematically in FIG. 3B, the individual body structures, such as, for example, Hip, Femur Left and Femur Right can be identified as individual elements. As shown in FIG. 3C, coordinate systems can be assigned to the individual, segmented structures. The coordinate systems can enable the structures to be virtually aligned in the neutral position shown in FIG. 3D.

Although the invention has been described using a hip joint by way of example, it is clear that the device and method in accordance with the invention can also be used to ascertain aperture angles for other joints, for example a knee joint or an elbow joint.

Although particular embodiments of the invention have been described in detail, it is understood that the invention is not limited correspondingly in scope, but includes all changes, modifications and equivalents coming within the spirit and terms of the claims appended hereto.

What is claimed is:

1. A device for determining a spatial angle formed by a joint, the device comprising:
   a detection device configured to detect (i) positions of joint components and/or (ii) positions of structures connected to or to be connected to the joint; and
   a computational unit programmed with a program configured to run on the computational unit, wherein the program is configured to ascertain a spatial angle formed by the joint based on the detected positions using joint geometry data stored in a database.

2. The device as set forth in claim 1, further comprising a storage unit for storing the database, the database having (i) a geometric structure of the joint and/or (ii) reference values for determining the spatial angle formed by the joint.

3. The device as set forth in claim 1, further comprising a robot and a force measuring device configured to apply defined forces in defined directions onto the joint.

4. The device as set forth in claim 1, wherein the detection device is configured to detect reference markers connected to the joint components and/or the structures connected to or to be connected to the joint.

5. The device as set forth in claim 1, wherein the computational unit is further configured to visually depict the spatial angle formed by the joint on an associated display.

6. The device as set forth in claim 1, further comprising a data output device configured to output the spatial angle formed by the joint.

7. The device as set forth in claim 1, further comprising a display, wherein the computational device provides a visual representation of the spatial angle formed by the joint for viewing on the display.

8. The device as set forth in claim 1, wherein the spatial angle formed by the joint comprises a spatial angle between a fixed upper leg axis and a plane or axis defined by a position of a patient's hip.

* * * * *